(12) United States Patent
Williams et al.

(10) Patent No.: US 6,735,649 B2
(45) Date of Patent: May 11, 2004

(54) MULTIPLE BUFFERS FOR REMOVING UNWANTED HEADER INFORMATION FROM RECEIVED DATA PACKETS

(75) Inventors: Robert Williams, Cupertino, CA (US); Kishore Karighattam, Cupertino, CA (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 519 days.

(21) Appl. No.: 09/848,652

(22) Filed: May 3, 2001

(65) Prior Publication Data

US 2002/0166006 A1 Nov. 7, 2002

(51) Int. Cl.[7] .............................................. G06F 13/00
(52) U.S. Cl. .............................. 710/65; 710/7; 710/33; 710/52; 710/53; 710/56
(58) Field of Search ............................... 710/33, 7, 52, 710/53, 56, 65

(56) References Cited

U.S. PATENT DOCUMENTS 5,881,242 A   3/1999   Ku et al. ............... 395/200.68

FOREIGN PATENT DOCUMENTS

EP   0574140 A1   12/1993

OTHER PUBLICATIONS

Jason Trachewsky. "Attaining Fast, Scaleable Home Networks," *CommsDesign—An EE Times Community*, via Internet at www.commsdesign.com/design_center/home-networking/OEG20010221S0081, Mar. 2001, pp. 1–11.

Khiem Le et al. "Adaptive Header ComprEssion (ACE) for Real–Time Multimedia," *Nokia Research Center*, Mar. 2000, pp. 1–38.

*Primary Examiner*—Jeffrey Gaffin
*Assistant Examiner*—Mohammad O. Farooq
(74) *Attorney, Agent, or Firm*—Winstead Sechrest & Minick P.C.

(57) ABSTRACT

A method for removing unwanted header information from a frame in a network is disclosed. It includes: storing beginning bytes of the frame in a first buffer and remaining bytes in a second buffer, where a size of the first buffer is smaller than the second buffer; determining that the unwanted header information is stored in the first buffer; copying bytes of the frame after the unwanted header information that are stored in the first buffer over the unwanted header information; reporting a number of bytes of the frame stored in the first buffer to be retrieved; and retrieving the reported number of bytes of the frame stored in the first buffer and the bytes of the frame stored in the second buffer. The copying of bytes occurs exclusively in the first buffer. Thus, removing the unwanted header information requires fewer processor cycles and minimizes latency in the packet receive process.

22 Claims, 8 Drawing Sheets

MULTIPLE BUFFERS FOR REMOVING UNWANTED HEADER INFORMATION FROM RECEIVED DATA PACKETS

FIELD OF THE INVENTION

The present invention relates to received data packets in a network, and more particularly to the removing unwanted header information from received data packets in the network.

BACKGROUND OF THE INVENTION

Home networks are becoming more common and desirable for connecting computers within a home. One type of home network is the home phone line network which uses telephone lines typically installed in residence homes for communication between computers in the home. The Home Phone Line Networking Alliance (HPNA) has published a specification to standardize the behavior of home phone line networks.

FIG. 1 illustrates the frame format according to the HPNA standard version 2.0. The frame includes a known 64 symbol preamble 102 and frame control bits 104. The frame control bits 104 include information concerning the modulation format and other miscellaneous control information, such as cyclical redundancy check (CRC) bits. The frame also includes a six-byte destination address 106, a six-byte source address 108, an eight-byte limited automatic repeat request (LARQ) 110, a four-byte Q Tag 112, and a two-byte length/type information 114. The LARQ 110 conveys link layer priority information and provides a negative acknowledgment protocol to increase the speed of frame retransmission. The Q Tag 112 contains information which may be used to prioritize data frames. The preamble 102 through the Q Tag 112 comprise the "header" of the frame. The remainder of the frame comprise the data 116, which can be between 46 to 1500 bytes. The data 116 is followed by four bytes of frame check sequence (FCS) 118, which is used to check for errors in the frame. A frame need not have both the LARQ 110 and the Q Tag 112. The frame may have the LARQ 110 without the Q Tag 112, the Q Tag 112 without the LARQ 110, or neither the LARQ 110 nor the Q Tag 112.

FIG. 2 illustrates a typical hardware-software interface for a home phone line network. The interface comprises a HPNA-compatible network interface controller (NIC) 206 which receives frames from a phone line. The NIC 206 sends the frame to a HPNA-compatible driver software 204 which is typically on a host computer. The driver software 204 then sends the frame to an upper layer software 202, such as the Network Driver Interface Specification (NDIS).

However, the upper layer 202 may not understand the LARQ 110 and/or the Q Tag 112 and erroneously see the frame as invalid. Thus, before the driver software 204 passes the frame to the upper layer software 202, the LARQ 110 and the Q Tag 112 must be removed from the frame.

Conventionally, when the NIC 206 forwards a frame, the frame is stored in a single buffer in the upper layer 202. Typically, to remove the LARQ 110 and the Q Tag 112 from the frame, all of the bytes before and after the LARQ 110 and Q Tag 112 are copied to a separate buffer without gaps between the bytes. However, copying all of these bytes wastes valuable processor cycles and adds unwanted latency to the packet receive process.

Accordingly, there exists a need for an improved method and system for removing unwanted header information from a frame in a network. The present invention addresses such a need.

SUMMARY OF THE INVENTION

A method for removing unwanted header information from a frame in a network is disclosed. It includes: storing beginning bytes of the frame in a first buffer and remaining bytes in a second buffer, where a size of the first buffer is smaller than the second buffer; determining the unwanted header information is stored in the first buffer; copying bytes of the frame after the unwanted header information which are stored in the first buffer over the unwanted header information; reporting a number of bytes of the frame stored in the first buffer to be retrieved; and retrieving the reported number of bytes of the frame stored in the first buffer and the bytes of the frame stored in the second buffer. The copying of bytes occur exclusively in the first buffer. Thus, removing the unwanted header information requires fewer processor cycles and minimizes latency in the packet receive process.

DETAILED DESCRIPTION

The present invention provides an improved method and system for removing unwanted header information from a frame in a network. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. Thus, the present invention is not intended to be limited to the embodiment shown but is to be accorded the widest scope consistent with the principles and features described herein.

To more particularly describe the features of the present invention, please refer to FIGS. 3 through 8 in conjunction with the discussion below.

The method and system in accordance with the present invention use a first and a second buffer to store each frame in the network. The first buffer is smaller in size than the second buffer. The copying of bytes to remove the limited automatic repeat request (LARQ) and the Q Tag from the frame occur exclusively in the smaller buffer. When the frame is forwarded to the upper layer 202, neither the preamble 102 or the frame control 104 is forwarded. Instead, only the portion of the frame that starts with the destination address 106 and ends with the FCS 118 is forwarded to the upper layer 202. The beginning bytes of the frame are stored in the first buffer until the first buffer is full. The remaining bytes of the frame are stored in the second buffer.

Figure 1:
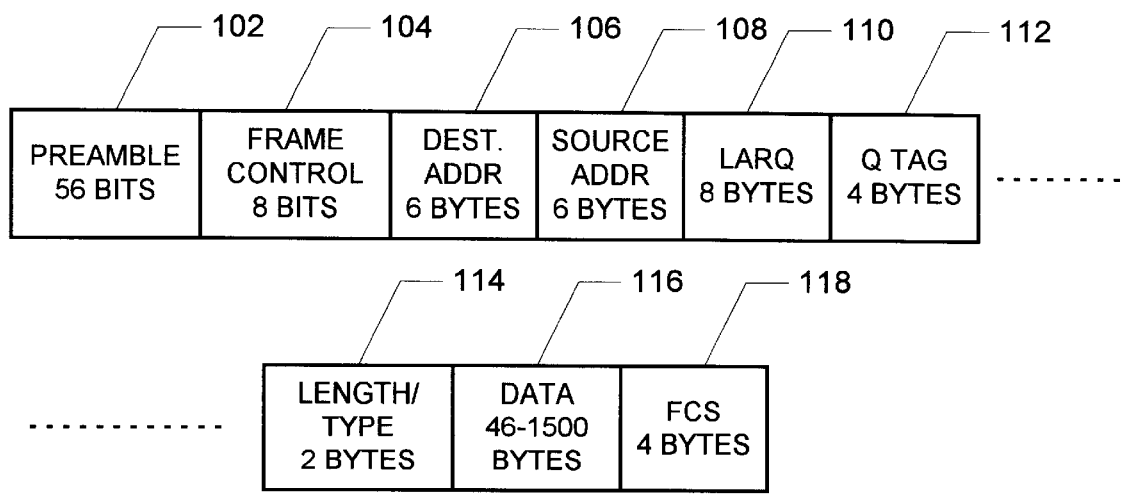
FIG. 1 illustrates the frame format according to the HPNA standard version 2.0.
Figure 2:
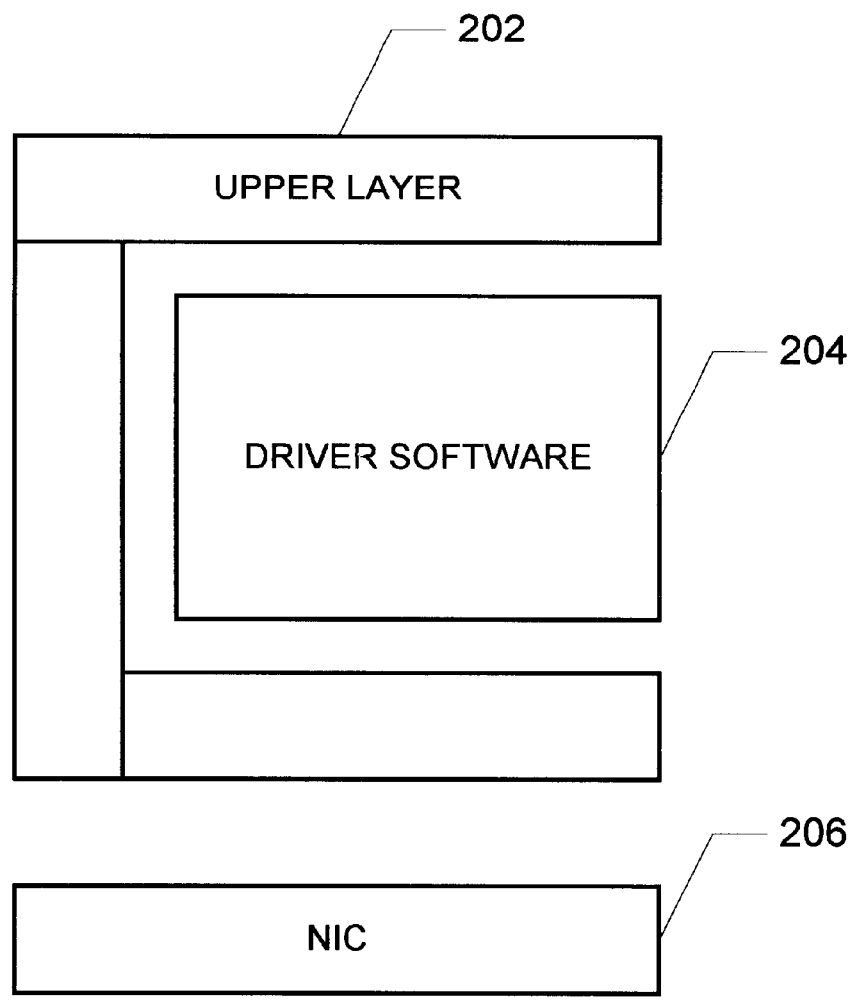
FIG. 2 illustrates a typical hardware-software interface for a home phone line network.
Figure 3:
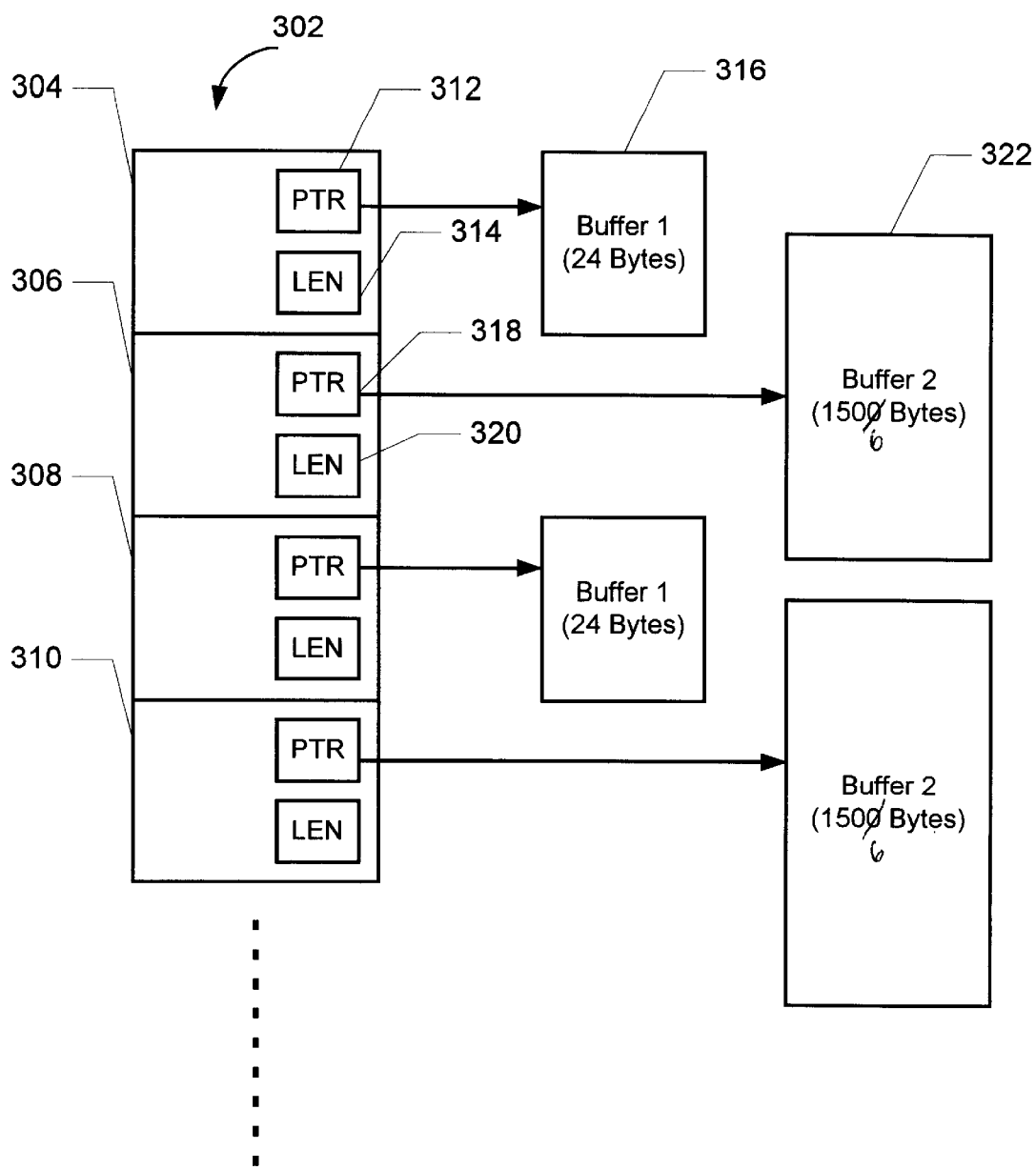
FIG. 3 illustrates a preferred embodiment of a receive descriptor ring utilized by the method and system in accordance with the present invention.

In the preferred embodiment, the first and second buffers are managed by a receive descriptor ring. FIG. 3 illustrates a preferred embodiment of a receive descriptor ring utilized by the method and system in accordance with the present invention. The receive descriptor ring 302 comprises a plurality of descriptors 304–310. The first descriptor 304 has a pointer 312 which points to a first buffer 316 and a length 314 of the first buffer 316. In the preferred embodiment, the first buffer has a size of 24 bytes, which is the largest possible size header, i.e., 106–112. The second descriptor 306 has a pointer 318 which points to a second buffer 322 and a length 320 of the second buffer 322. In the preferred embodiment, the second buffer has a size of 1506 bytes, which is the largest possible size length/type 114, data 116, and frame check sequence (FCS) 118. As a frame is received, the first 24 bytes are stored in the first buffer 316 with the remaining bytes stored in the second buffer 322. The first 24 bytes of the next frame is then stored in the buffer pointed to by the next descriptor 308, with the remaining bytes stored in the buffer pointed to by the descriptor 310, and so forth. Once the buffers pointed to by each of the descriptors are used, the receive process returns to the first descriptor 304 and reuses the buffers. Thus, the receive descriptor data structure 302 is a "ring".

Figure 4:
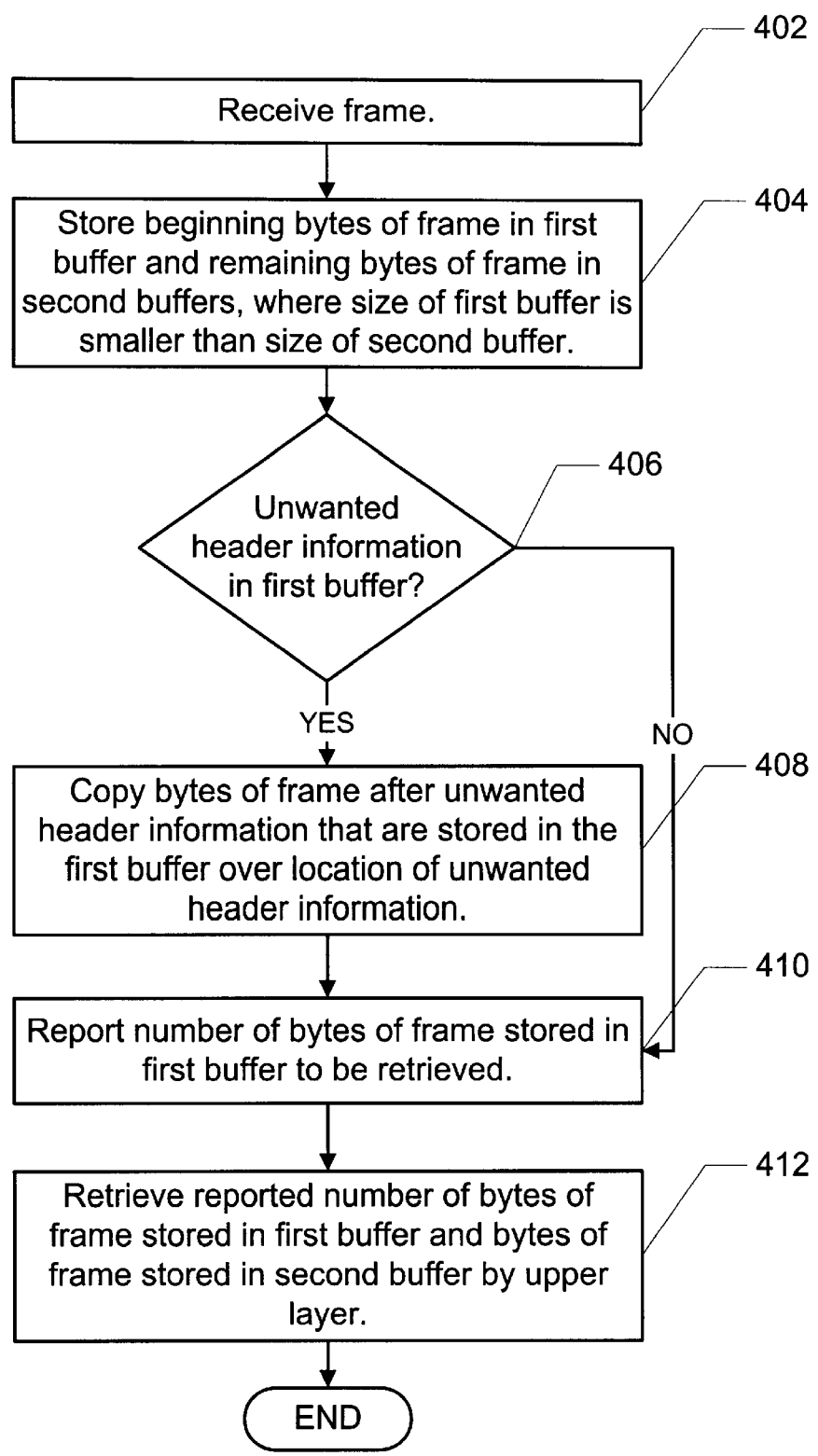
FIG. 4 is a flowchart illustrating a preferred embodiment of the method for removing unwanted header information from a frame in a network in accordance with the present invention.

FIG. 4 is a flowchart illustrating a preferred embodiment of the method for removing unwanted header information from a frame in a network in accordance with the present invention. First, the frame is received, via step 402. The beginning bytes of the frame are stored in the first buffer 316, and the remaining bytes are stored in the second buffer 322, via step 404. The size of the first buffer 316 is smaller than the second buffer 322. The sizes of the buffers 316, 322 are set such that the header is stored exclusively in the first buffer 316. The driver software 204 then examines the bytes stored in the first buffer 316 and determines if it contains any unwanted header information, via step 406. Unwanted header information includes the LARQ 110 and/or the Q Tag 112. The driver software 204 then copies the bytes of the frame after the unwanted header information which are stored in the first buffer 316 over the location of the unwanted header information, via step 408. It then reports the number of bytes of the frame stored in the first buffer 316 to be retrieved, via step 410. This report is necessary since the frame bytes stored in the first buffer 316 after the copying can be less than the size of the buffer 316. The upper layer 202 then retrieves the reported number of bytes of the frame stored in the first buffer 316 and the bytes of the frame stored in the second buffer 322, via step 412, without gaps between the bytes from the two buffers 316, 322.

FIGS. 5 through 8 illustrate examples of the method for removing unwanted header information from a frame in a network in accordance with the present invention. In the preferred embodiment, the header contains one of four possible scenarios: (1) the LARQ 110 and the Q Tag 112; (2) the LARQ 110 but not the Q Tag 112; (3) the Q Tag 112 but not the LARQ 110; or (4) neither the LARQ 110 nor the Q Tag 112.

Figure 5:
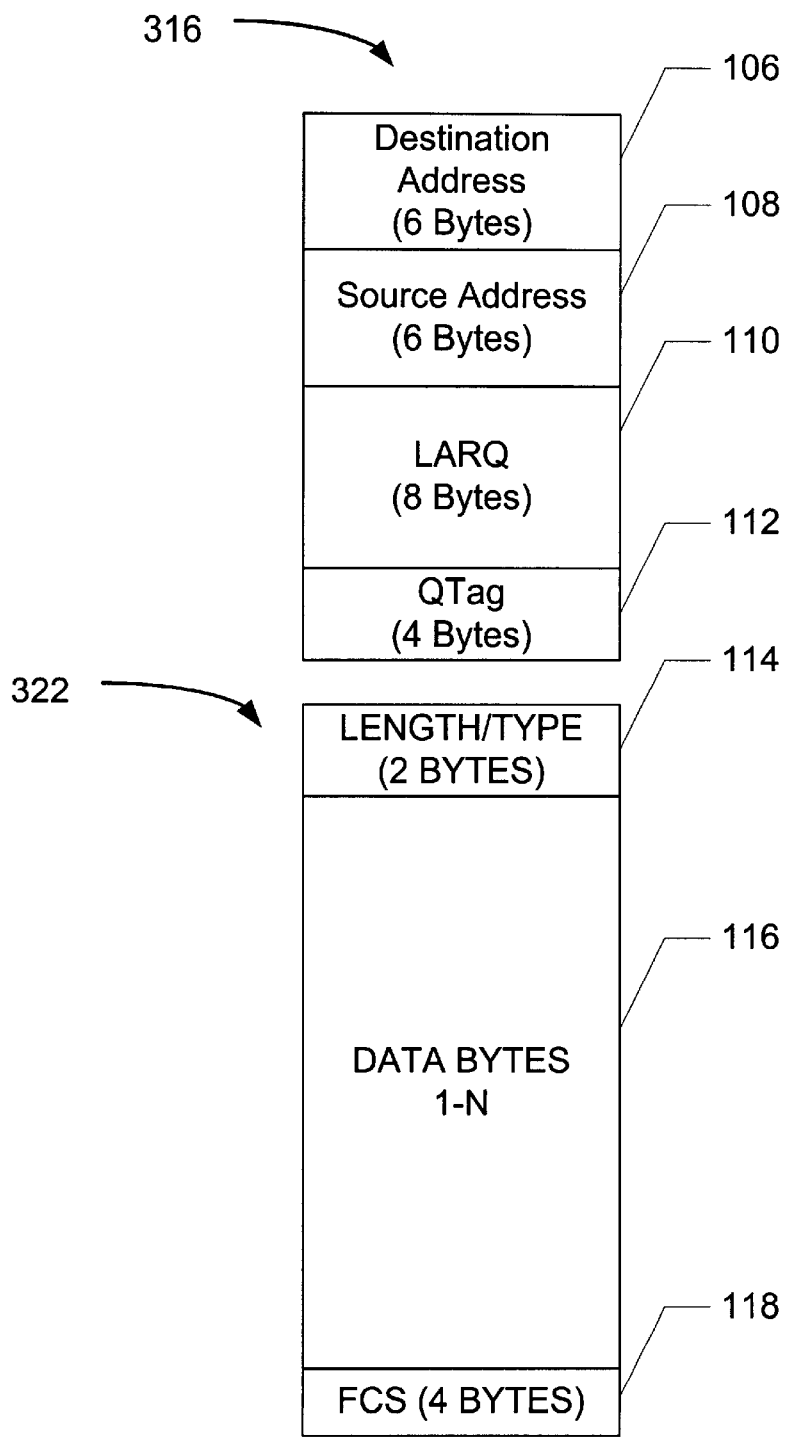
FIGS. 5 through 8 illustrate examples of the method for removing unwanted header information from a frame in a network in accordance with the present invention.

FIG. 5 illustrates the first scenario where the header contains the LARQ 110 and the Q Tag 112. When the frame is received, via step 402, the first 24 bytes of the frame are stored in the first buffer 316, and the remaining bytes of the frame are stored in the second buffer 322, via step 404. Thus, the first buffer 316 contains the six-byte destination address 106, the 6-byte source address 108, the eight-byte LARQ 110, and the four-byte Q Tag 112. The second buffer 318 contains the two-byte length/type 114, n-bytes of data 116, and the four-byte FCS 118. The driver software 204 examines the bytes in the first buffer 316 and determines that it contains unwanted header information, i.e., the LARQ 110 and the Q Tag 112, via step 406. Because no bytes of the frame that come after the LARQ 110 and the Q Tag 112 are stored in the first buffer 316, no copying, via step 408, is performed. The driver software 204 then reports the number of bytes of the frame stored in the first buffer 316, via step 410. For the scenario illustrated in FIG. 5, the number of bytes is twelve, i.e., six bytes of the destination address 106 plus six bytes of the source address 108. The upper layer 202 then retrieves the reported number of bytes of the frame stored in the first buffer 316, i.e., the first twelve bytes, and the bytes of the frame stored in the second buffer 322, via step 412. Thus, the retrieved bytes are the destination address 106, the source address 108, the length/type 114, the data 116, and the FCS 118. The LARQ 110 and the Q Tag 112 are thus removed from the frame retrieved by the upper layer 202.

Figure 6:
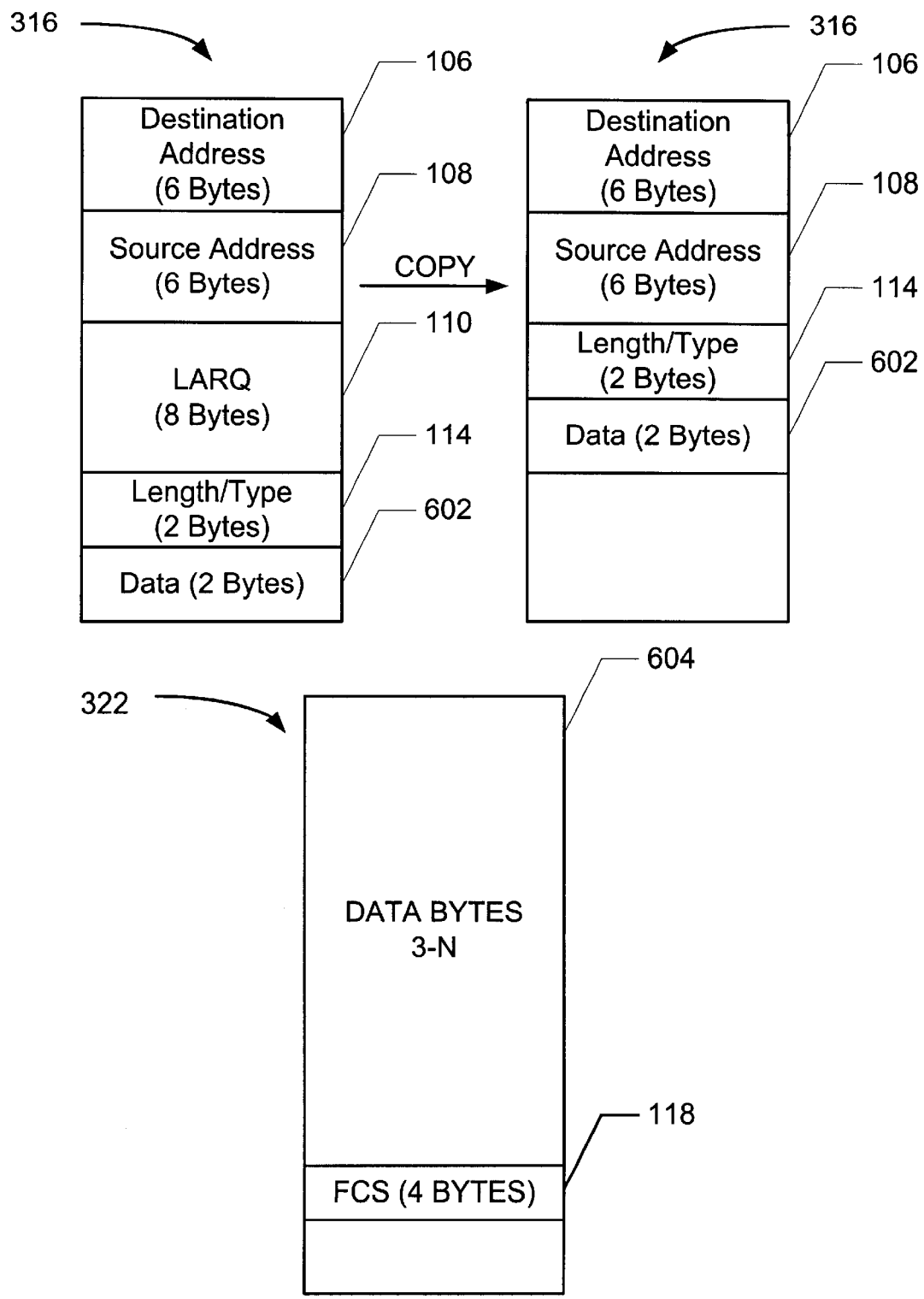

FIG. 6 illustrates the second scenario where the header contains the LARQ 110 but not the Q Tag 112. When the frame is received, via step 402, the first 24 bytes of the frame are stored in the first buffer 316, and the remaining bytes of the frame are stored in the second buffer 322, via step 404. Thus, the first buffer 316 contains the six-byte destination address 106, the 6-byte source address 108, the eight-byte LARQ 110, the two-byte length/type 114, and the first two bytes 602 of the data 116. The second buffer 322 contains the remaining bytes 604 of the data 116 and the four-byte FCS 118. The driver software 204 examines the bytes stored in the first buffer 316 and determines that it contains unwanted header information, i.e., the LARQ 110, via step 406. The driver software 204 next copies the bytes of the frame after the LARQ 110 which are stored in the first buffer 316 over the LARQ 110, via step 408. For this scenario, the length/type 114 and the data bytes 602 are copied over the LARQ 110. The driver software 204 then reports the number of bytes of the frame stored in the first buffer 316, via step 410. For the scenario illustrated in FIG. 6, the number of bytes is sixteen, i.e., six bytes of the destination address 106, six bytes of the source address 108, two bytes of the length/type 114, and two bytes 602 of the data 116. The upper layer 202 then retrieves the reported number of bytes of the frame stored in the first buffer 316, i.e., the first sixteen bytes, and the bytes of the frame stored in the second buffer 322, via step 412. Thus, the retrieved bytes are the destination address 106, the source address 108, the length/type 114, the data 116, and the FCS 118. The LARQ 110 is thus removed from the frame retrieved by the upper layer 202.

Figure 7:
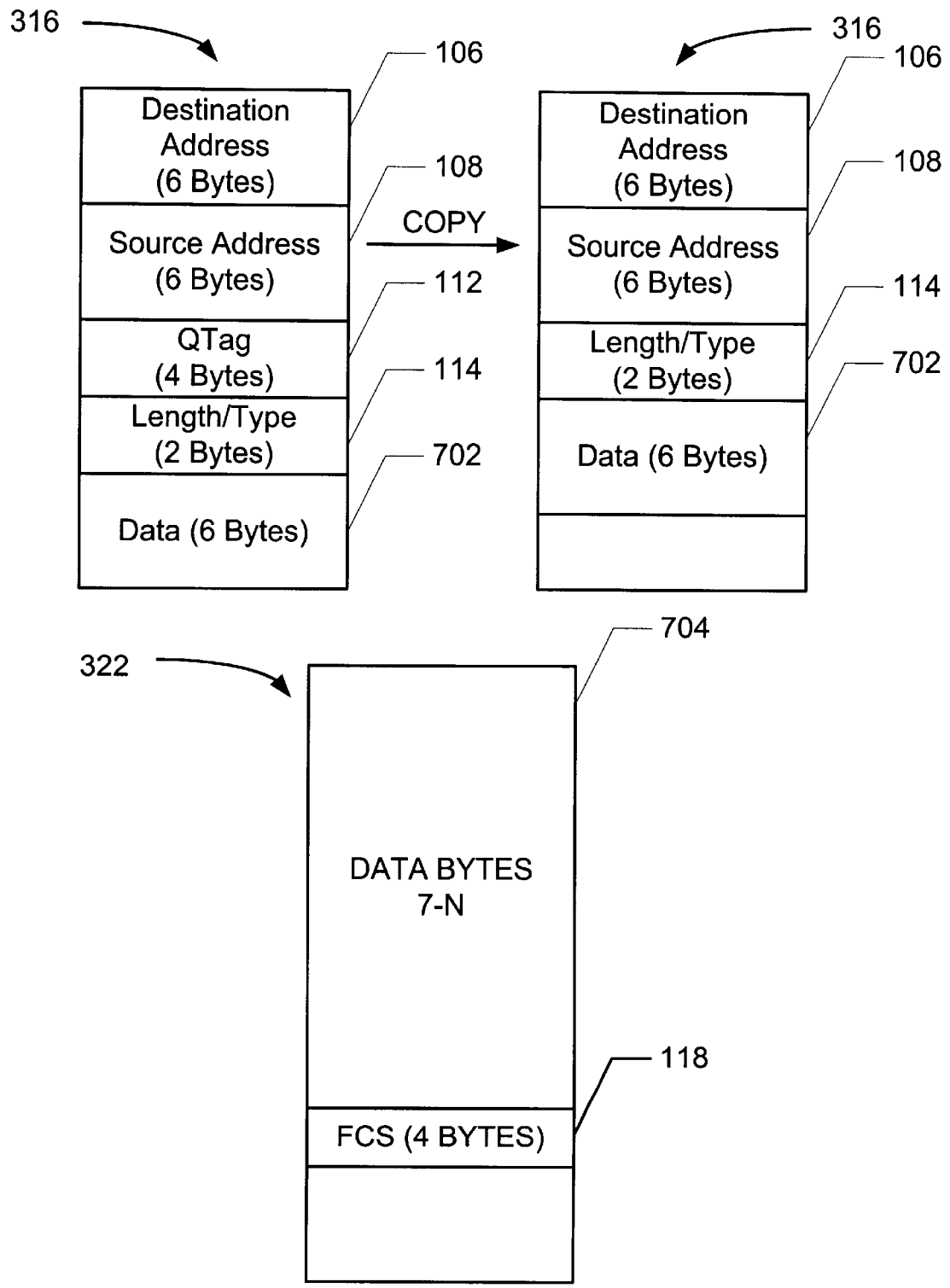

FIG. 7 illustrates the third scenario where the header contains the Q Tag 112 but not the LARQ 110. When the frame is received, via step 402, the first 24 bytes of the frame are stored in the first buffer 316, and the remaining bytes of the frame are stored in the second buffer 322, via step 402. Thus, the first buffer 316 contains the six-byte destination address 106, the 6-byte source address 108, the four-byte Q Tag 112, the two-byte length/type 114, and the first six bytes 702 of the data 116. The second buffer 318 contains the remaining bytes 704 of the data 116 and the four-byte FCS 118. The driver software 204 examines the bytes stored in the first buffer 316 and determines that it contains unwanted header information, i.e., the Q Tag 112, via step 406. The driver software 204 next copies the bytes of the frame after the Q Tag 112 that are stored in the first buffer 316 over the Q Tag 112, via step 408. For this scenario, the length/type 114 and the data bytes 702 are copied over the Q Tag 112. The driver software 204 then reports the number of bytes of the frame stored in the first buffer 316, via step 410. For the scenario illustrated in FIG. 7, the number of bytes is 20, i.e., six bytes of the destination address 106, six bytes of the source address 108, two bytes of the length/type 114, and six bytes 702 of the data 116. The upper layer 202 then retrieves the reported number of bytes of the frame stored in the first buffer 316, i.e., the first 20 bytes, and the bytes of the frame stored in the second buffer 318, via step 412. Thus, the retrieved bytes are the destination address 106, the source address 108, the length/type 114, the data 116, and the FCS 118. The Q Tag 112 is thus removed from the frame retrieved by the upper layer 202.

Figure 8:
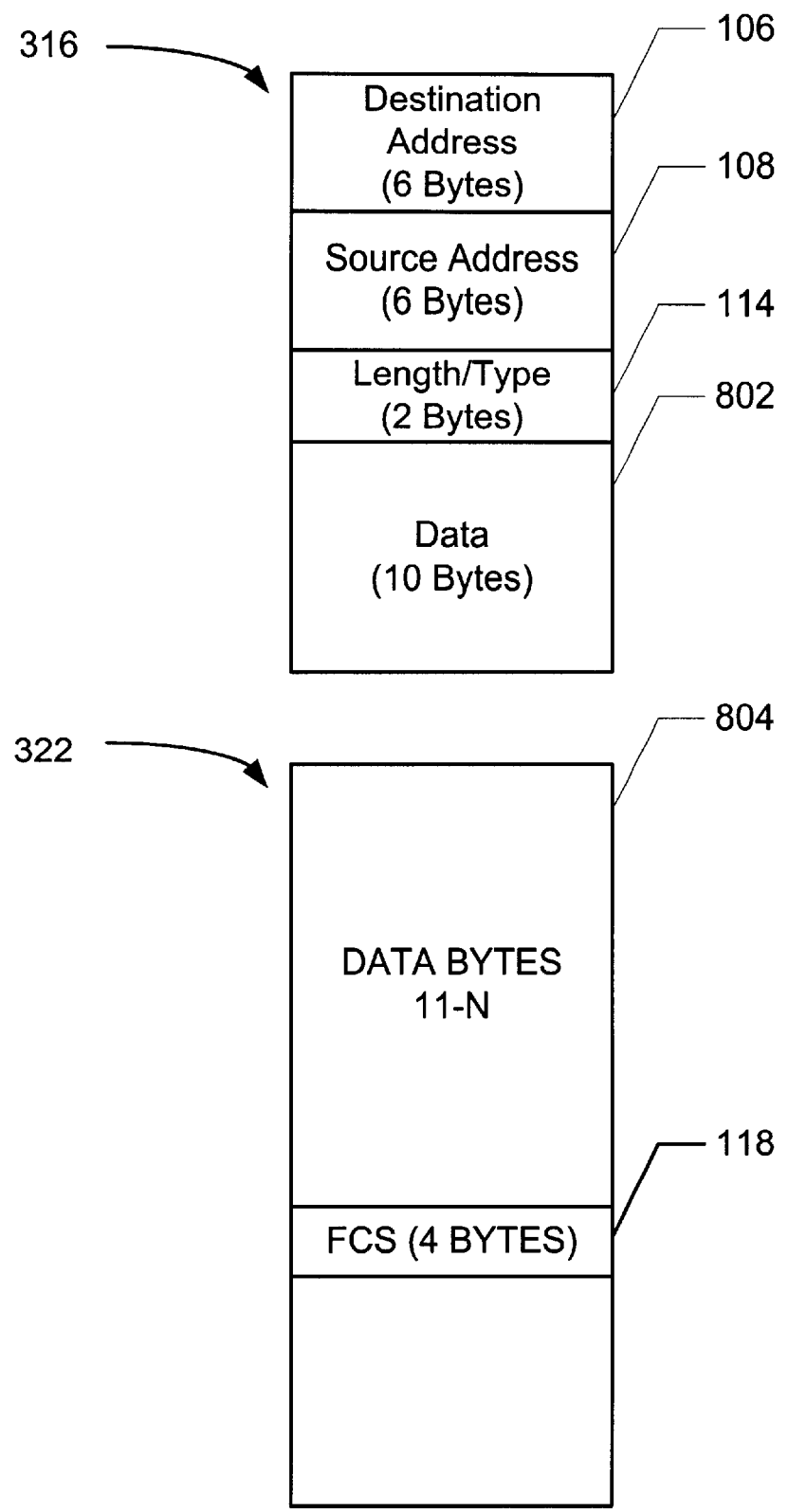

FIG. 8 illustrates the fourth scenario where the header contains neither the LARQ 110 nor the Q Tag 112. When the frame is received, via step 402, the first 24 bytes of the frame are stored in the first buffer 316, and the remaining bytes of the frame are stored in the second buffer 322, via step 404. Thus, the first buffer 316 contains the six-byte destination address 106, the 6-byte source address 108, the two-byte length/type 114, and the first ten bytes 802 of the data 116. The second buffer 318 contains the remaining bytes 804 of the data 116 and the four-byte FCS 118. The driver software 204 examines the bytes stored in the first buffer 316 and determines that it does not contain any unwanted header information, via step 406. The driver software 204 then reports the number of bytes of the frame stored in the first buffer 316, via step 410. For the scenario illustrated in FIG. 8, the number of bytes is 24, i.e., six bytes of the destination address 106, six bytes of the source address 108, two bytes of the length/type 114, and 10 bytes 802 of the data 116. The upper layer 202 then retrieves the reported number of bytes of the frame stored in the first buffer 316, i.e., 24 bytes, and the bytes of the frame stored in the second buffer 322, via step 412. Thus, the retrieved bytes are the destination address 106, the source address 108, the length/type 114, the data 116, and the FCS 118.

An improved method and system for removing unwanted header information from a frame in a network has been disclosed. The present invention uses a first and a second buffer to store each frame in the network. The first buffer is smaller in size than the second buffer. The copying of bytes to remove the unwanted header information from the frame occurs exclusively in the smaller buffer. In this manner, the removal of the unwanted header information requires fewer processor cycles and minimizes the latency in the packet receive process.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A method for removing unwanted header information from a frame in a network, comprising the steps of:
   (a) receiving the frame;
   (b) storing beginning bytes of the frame in a first buffer and storing remaining bytes of the frame in a second buffer, wherein a size of the first buffer is smaller than a size of the second buffer;
   (c) determining the unwanted header information is stored in the first buffer;
   (d) copying bytes of the frame after the unwanted header information that are stored in the first buffer over a location of the unwanted header information;
   (e) reporting a number of bytes of the frame stored in the first buffer to be retrieved; and
   (f) retrieving the reported number of bytes of the frame stored in the first buffer and retrieving the bytes of the frame stored in the second buffer, wherein the storing step (b) comprises:
      (1) storing a destination address in the first buffer;
      (2) storing a source address in the first buffer;
      (3) storing a limited automatic repeat request (LARQ) in the first buffer;
      (4) storing a Q Tag in the first buffer;
      (5) storing a length/type in the second buffer;
      (6) storing a plurality of data bytes in the second buffer; and
      (7) storing a frame check sequence (FCS) in the second buffer.

2. The method of claim 1, wherein the determining step (c) comprises:
   (c1) determining that the LARQ and the Q Tag are stored in the first buffer.

3. The method of claim 1, wherein the reporting step (e) comprises:
   (e1) reporting a number of bytes for the destination address and the source address stored in the first buffer.

4. The method of claim 1, wherein the retrieving step (f) comprises:
   (f1) retrieving the destination address and the source address stored in the first buffer; and
   (f2) retrieving the length/type, the plurality of data bytes, and the FCS stored in the second buffer.

5. A method for removing unwanted header information from a frame in a network, comprising the steps of
   (a) receiving the frame;
   (b) storing beginning bytes of the frame in a first buffer and storing remaining bytes of the frame in a second buffer, wherein a size of the first buffer is smaller than a size of the second buffer;
   (c) determining the unwanted header information is stored in the first buffer;
   (d) copying bytes of the frame after the unwanted header information that are stored in the first buffer over a location of the unwanted header information;
   (e) reporting a number of bytes of the frame stored in the first buffer to be retrieved; and
   (f) retrieving the reported number of bytes of the frame stored in the first buffer and retrieving the bytes of the frame stored in the second buffer, wherein the storing step (b) comprises:
      (1) storing a destination address in the first buffer;
      (2) storing a source address in the first buffer;
      (3) storing a LARQ in the first buffer;
      (4) storing a length/type in the first buffer;
      (5) storing beginning bytes of a plurality of data bytes in the first buffer;
      (6) storing remaining bytes of the plurality of data bytes in the second buffer; and
      (7) storing a FCS in the second buffer.

6. The method of claim 5, wherein the determining step (c) comprises:
   (c1) determining that the LARQ is stored in the first buffer.

7. The method of claim 5, wherein the copying step (d) comprises:
   (d1) copying the length/type and the beginning bytes of the plurality of data bytes over the LARQ in the first buffer.

8. The method of claim 5, wherein the reporting step (e) comprises:

(e1) reporting a number of bytes for the destination address, the source address, the length/type, and the beginning bytes of the plurality of data bytes stored in the first buffer.

9. The method of claim 5, wherein the retrieving step (f) comprises:

(f1) retrieving the destination address, the source address, the length/type, and the beginning bytes of the plurality of data bytes stored in the first buffer; and (f2) retrieving the remaining bytes of the plurality of data bytes and the FCS stored in the second buffer.

10. A method for removing unwanted header information from a frame in a network, comprising the steps of (a) receiving the frame;

(b) storing beginning bytes of the frame in a first buffer and storing remaining bytes of the frame in a second buffer, wherein a size of the first buffer is smaller than a size of the second buffer;

(c) determining the unwanted header information is stored in the first buffer;

(d) copying bytes of the frame after the unwanted header information that are stored in the first buffer over a location of the unwanted header information;

(e) reporting a number of bytes of the frame stored in the first buffer to be retrieved; and (f) retrieving the reported number of bytes of the frame stored in the first buffer and retrieving the bytes of the frame stored in the second buffer, wherein the storing step (b) comprises:

(b1) storing a destination address in the first buffer;
(b2) storing a source address in the first buffer;
(b3) storing a Q Tag in the first buffer;
(b4) storing a length/type in the first buffer;
(b5) storing beginning bytes of a plurality of data bytes in the first buffer;
(b6) storing remaining bytes of the plurality of data bytes in the second buffer; and
(b7) storing a FCS in the second buffer.

11. The method of claim 10, wherein the determining step (c) comprises:

(c1) determining that the Q Tag is stored in the first buffer.

12. The method of claim 11, wherein the copying step (d) comprises:

(d1) copying the length/type and the beginning bytes of the plurality of data bytes over the Q Tag in the first buffer.

13. The method of claim 11, wherein the reporting step (e) comprises:

(e1) reporting a number of bytes for the destination address, the source address, the length/type, and the beginning bytes of the plurality of data bytes stored in the first buffer.

14. The method of claim 11, wherein the retrieving step (f) comprises:

(f1) retrieving the destination address, the source address, the length/type, and the beginning bytes of the plurality of data bytes stored in the first buffer; and (f2) retrieving the remaining bytes of the plurality of data bytes and the FCS stored in the second buffer.

15. A method for removing unwanted header information from a frame in a network, comprising the steps of:

(a) receiving the frame;

(b) storing beginning bytes of the frame in a first buffer and storing remaining bytes of the frame in a second buffer, wherein a size of the first buffer is smaller than a size of the second buffer;

(c) determining the unwanted header information is stored in the first buffer;

(d) copying bytes of the frame after the unwanted header information that are stored in the first buffer over a location of the unwanted header information;

(e) reporting a number of bytes of the frame stored in the first buffer to be retrieved; and (f) retrieving the reported number of bytes of the frame stored in the first buffer and retrieving the bytes of the frame stored in the second buffer, wherein the storing step (b) comprises:

(b1) storing a destination address in the first buffer;
(b2) storing a source address in the first buffer;
(b3) storing a length/type in the first buffer;
(b4) storing beginning bytes of a plurality of data bytes in the first buffer;
(b5) storing remaining bytes of the plurality of data bytes in the second buffer; and
(b6) storing a FCS in the second buffer.

16. The method of claim 15, wherein the determining step (c) comprises:

(c1) determining that no unwanted header information is stored in the first buffer.

17. The method of claim 15, wherein the reporting step (e) comprises:

(e1) reporting a number of bytes for the destination address, the source address, the length/type, and the beginning bytes of the plurality of data bytes stored in the first buffer.

18. The method of claim 15, wherein the retrieving step (f) comprises:

(f1) retrieving the destination address, the source address, the length/type, and the beginning bytes of the plurality of data bytes stored in the first buffer; and (f2) retrieving the remaining bytes of the plurality of data bytes and the FCS stored in the second buffer.

19. A computer readable medium with computer instructions for removing unwanted header information from a frame in a network, the instructions for:

(a) receiving the frame;

(b) storing beginning bytes of the frame in a first buffer and storing remaining bytes of the frame in a second buffer, wherein a size of the first buffer is smaller than a size of the second buffer;

(c) determining the unwanted header information is stored in the first buffer;

(d) copying bytes of the frame after the unwanted header information that are stored in the first buffer over a location of the unwanted header information;

(e) reporting a number of bytes of the frame stored in the first buffer to be retrieved; and (f) retrieving the reported number of bytes of the frame stored in the first buffer and retrieving the bytes of the frame stored in the second buffer, wherein the storing instructions (b) comprise:

(b1) storing a destination address in the first buffer;
(b2) storing a source address in the first buffer;
(b3) storing a limited automatic repeat request (LARQ) in the first buffer;
(b4) storing a Q Tag in the first buffer;
(b5) storing a length/type in the second buffer;
(b6) storing a plurality of data bytes in the second buffer; and (b7) storing a frame check sequence (FCS) in the second buffer.

20. A computer readable medium with computer instructions for removing unwanted header information from a frame in a network, the instructions for:

(a) receiving the frame;

(b) storing beginning bytes of the frame in a first buffer and storing remaining bytes of the frame in a second buffer, wherein a size of the first buffer is smaller than a size of the second buffer;

(c) determining the unwanted header information is stored in the first buffer;

(d) copying bytes of the frame after the unwanted header information that are stored in the first buffer over a location of the unwanted header information;

(e) reporting a number of bytes of the frame stored in the first buffer to be retrieved; and (f) retrieving the reported number of bytes of the frame stored in the first buffer and retrieving the bytes of the frame stored in the second buffer, wherein the storing instructions (b) comprise:

(b1) storing a destination address in the first buffer;
(b2) storing a source address in the first buffer;
(b3) storing a LARQ in the first buffer;
(b4) storing a length/type in the first buffer;
(b5) storing beginning bytes of a plurality of data bytes in the first buffer;
(b6) storing remaining bytes of the plurality of data bytes in the second buffer; and
(b7) storing a FCS in the second buffer.

21. A system for removing unwanted header information from a frame in a network, comprising:

(a) circuitry for receiving the frame;

(b) circuitry for storing beginning bytes of the frame in a first buffer and storing remaining bytes of the frame in a second buffer, wherein a size of the first buffer is smaller than a size of the second buffer;

(c) circuitry for determining the unwanted header information is stored in the first buffer;

(d) circuitry for copying bytes of the frame after the unwanted header information that are stored in the first buffer over a location of the unwanted header information;

(e) circuitry for reporting a number of bytes of the frame stored in the first buffer to be retrieved; and (f) circuitry for retrieving the reported number of bytes of the frame stored in the first buffer and retrieving the bytes of the frame stored in the second buffer, wherein the storing circuitry (b) comprises:

(b1) circuitry for storing a destination address in the first buffer;
(b2) circuitry for storing a source address in the first buffer;
(b3) circuitry for storing a LARQ in the first buffer;
(b4) circuitry for storing a length/type in the first buffer;
(b5) circuitry for storing beginning bytes of a plurality of data bytes in the first buffer;
(b6) circuitry for storing remaining bytes of the plurality of data bytes in the second buffer; and
(b7) circuitry for storing a FCS in the second buffer.

22. A system for removing unwanted header information from a frame in a network, comprising:

(a) circuitry for receiving the frame;

(b) circuitry for storing beginning bytes of the frame in a first buffer and storing remaining bytes of the frame in a second buffer, wherein a size of the first buffer is smaller than a size of the second buffer;

(c) circuitry for determining the unwanted header information is stored in the first buffer;

(d) circuitry for copying bytes of the frame after the unwanted header information that are stored in the first buffer over a location of the unwanted header information;

(e) circuitry for reporting a number of bytes of the frame stored in the first buffer to be retrieved; and (f) circuitry for retrieving the reported number of bytes of the frame stored in the first buffer and retrieving the bytes of the frame stored in the second buffer, wherein the storing circuitry (b) comprises:

(b1) circuitry for storing a destination address in the first buffer;
(b2) circuitry for storing a source address in the first buffer;
(b3) circuitry for storing a Q Tag in the first buffer;
(b4) circuitry for storing a length/type in the first buffer;
(b5) circuitry for storing beginning bytes of a plurality of data bytes in the first buffer;
(b6) circuitry for storing remaining bytes of the plurality of data bytes in the second buffer; and
(b7) circuitry for storing a FCS in the second buffer.

* * * * *

UNITED STATES PATENT AND TRADEMARK OFFICE
CERTIFICATE OF CORRECTION

PATENT NO. : 6,735,649 B2
DATED : May 11, 2004
INVENTOR(S) : Robert Williams and Kishore Karighattam It is certified that error appears in the above-identified patent and that said Letters Patent is hereby corrected as shown below:

Column 6,
Line 5, please replace "(1)" with -- (b1) --.
Line 6, please replace "(2)" with -- (b2) --.
Line 7, please replace "(3)" with -- (b3) --.
Line 9, please replace "(4)" with -- (b4) --.
Line 10, please replace "(5)" with -- (b5) --.
Line 11, please replace "(6)" with -- (b6) --.
Line 13, please replace "(7)" with -- (b7) --.
Line 30, following "of" please insert -- : --.
Line 47, please replace "(1)" with -- (b1) --.
Line 48, please replace "(2)" with -- (b2) --.
Line 49, please replace "(3)" with -- (b3) --.
Line 50, please replace "(4)" with -- (b4) --.
Line 51, please replace "(5)" with -- (b5) --.
Line 53, please replace "(6)" with -- (b6) --.
Line 55, please replace "(7)" with -- (b7) --.

Signed and Sealed this

Twenty-seventh Day of July, 2004

JON W. DUDAS
*Acting Director of the United States Patent and Trademark Office*